US008323357B2

(12) United States Patent
Feldhues et al.

(10) Patent No.: US 8,323,357 B2
(45) Date of Patent: Dec. 4, 2012

(54) FLUORINE-SUBSTITUTED PERYLENES FOR COLOUR FILTERS IN LCDS

(75) Inventors: Ulrich Feldhues, Bergisch Gladbach (DE); Frank Linke, Köln (DE); Stephan Michaelis, Odenthal (DE); Dirk Pfuetzenreuter, Burscheid (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 12/752,425

(22) Filed: Apr. 1, 2010

(65) Prior Publication Data
US 2010/0264382 A1 Oct. 21, 2010

(30) Foreign Application Priority Data

Apr. 15, 2009 (EP) ..................... 09157914

(51) Int. Cl.
*C09B 67/20* (2006.01)
*C09B 67/22* (2006.01)
*C07D 471/22* (2006.01)

(52) U.S. Cl. ............... 8/637.1; 8/506; 546/37; 252/582; 252/586; 428/1.1; 428/1.31; 359/885

(58) Field of Classification Search ............... 546/37; 8/506, 637.1; 349/2; 359/885; 252/582, 252/586; 428/1.1, 1.31
See application file for complete search history.

(56) References Cited

U.S. PATENT DOCUMENTS

| 5,472,494 | A | * | 12/1995 | Hetzenegger et al. | ........ | 106/493 |
| 6,068,695 | A | | 5/2000 | Flatt et al. | | |
| 6,251,553 | B1 | | 6/2001 | Baur et al. | | |
| 6,596,446 | B2 | | 7/2003 | Wolf et al. | | |
| 2002/0034696 | A1 | * | 3/2002 | Wolf et al. | ......... | 430/7 |
| 2006/0135774 | A1 | * | 6/2006 | Weber et al. | ............ | 546/37 |
| 2007/0017416 | A1 | | 1/2007 | Feldhues et al. | | |
| 2008/0269485 | A1 | | 10/2008 | Moonen et al. | | |

FOREIGN PATENT DOCUMENTS

| EP | 0227980 | | 7/1987 |
| EP | 1843407 | | 10/2007 |
| JP | 11217514 | | 8/1999 |
| JP | 2002348493 | | 12/2002 |
| WO | WO 2004/074384 | * | 9/2004 |

OTHER PUBLICATIONS

The Derwent abstract for JP 2005211873, 2005.*
European Search Report from co-pending Application EP09157914 dated Nov. 6, 2009, 2 pages.
Römpp Lexikon, Lacke and Druckfarben, Dr. Ulrich Zorll, Thieme Verlage 1998, pp. 445-446, 491-492.

* cited by examiner

*Primary Examiner* — Lorna M Douyon
*Assistant Examiner* — Amina Khan
(74) *Attorney, Agent, or Firm* — Michael A. Miller

(57) ABSTRACT

The use of fluorine-substituted perylenes in color filters for liquid-crystal displays is described.

9 Claims, No Drawings

FLUORINE-SUBSTITUTED PERYLENES FOR COLOUR FILTERS IN LCDS

The invention relates to the use of fluorine-containing perylenes in colour filters for LCDs (liquid-crystal displays) and also to formulations of such colourants and to their use for producing colour filters, to the colour filters themselves, and also to new perylenes.

Colour filters are chiefly employed today in liquid-crystal displays and screens, colour resolution instruments and sensors. One known example are the flat screens on personal computers, televisions and video cameras. There are various ways to produce colour filters, which differ not only in the way the colours are applied but in the generation of the colour element patterns from the primary colours red, green and blue, as well as black. The colours may be applied, for example, by colouring a base layer (e.g. gelatine) by means of soluble dyes or pigments ("Dye Method", "Dye Dispersion Method"), screenprinting, offset printing or ink-jet printing of pigment pastes, pigment formulations or pigment inks, electrodeposition of photoresists based on dyes or pigments, and also, in particular, by means of the pigment dispersion method, which uses pigments dispersed either in a polyimide resin ("non-photosensitive polyimide method") or in a photoresist ("photosensitive acrylic method"). Associated with the stated methods, both the direct generation of the colour element patterns, by printing, and the indirect, photolithographic generation, are important, the latter in relation to the aforementioned pigment dispersion method in particular. The technique of the pigment dispersion method in the form of the "non-photosensitive polyimide method", for example, is disclosed in JP-A-11-217514 (1998).

In the case of the pigment dispersion method according to the photoresist method, the colour-imparting pigments are in fine distribution (dispersed) in a UV-curable photoresist. The photoresist, as well as the pigment, is generally composed, in this case, of the components binder resin, polymerizable monomer, photoinitiator and, optionally, a solvent. It is prepared by, for example, first finely dispersing the pigment in the form of a concentrate in solvent and, optionally, binder resin, and adjusting the dispersion immediately prior to application together with the monomer and the photoinitiator and any further components as well. The pigmented photoresist is applied uniformly to the substrate, glass for example, by means for example of the spincoating method, and is pre-dried, UV-exposed by means of the photomask, developed to the desired colour element patterns by means of a generally inorganic alkaline solution, and the coating is cleaned and optionally aftercured. This operation is repeated for each colour, i.e. generally three times for a trichromatism in the colours red, green and blue, for example.

The advantages associated with the use of pigments in conjunction with the pigment dispersion method lie in the improved light resistance, moisture resistance and temperature resistance of the colour filters as compared with dye-based coating systems. On the other hand, the transparency and colour purity of coatings based on pigments, irrespective of the coating method, are still unsatisfactory. Particularly when different pigments are incorporated in a mixture to shade the mixture to the desired colour locus values in the photoresist, there are unwanted losses in brilliance and transparency, with the result that operation of the displays or screens (LCDs) unavoidably entails an increased energy cost.

The use of pigments of the perylenetetracarboxylic diimide type such as C.I. Pigment Red 149 or diketopyrrolopyrrole type such as C.I. Pigment Red 254 or anthraquinones such as C.I. Pigment Red 177 in colour filters is known in principle.

The accompanying use of perylene pigments such as C.I. Pigment Red 149 is already mentioned, for example, together with other pigments, in colour filters, in EP-A-1146087.

EP 1004941 describes mixed crystals of quinacridones such as C.I. Pigment Violet 19 and C.I. Pigment Red 122 and their use inter alia for colour filters. Besides the sole specific mixed crystal, there is also a general mention of those with quinacridones substituted by fluorine on the quinacridone nucleus.

EP 1843407 discloses liquid-crystalline perylenes, substituted on the perylene nucleus by fluorine, as semiconductors for transistors and solar cells.

WO 2008/128934 discloses specific fluorine-containing perylenes and their use for EPDs (electrophoretic displays).

JP 2002348493 discloses mixtures of quinacridones optionally substituted by fluorine on the quinacridone nucleus, and their sulphonated derivatives, for colour filters. Some of these types of pigments already feature high lightfastness and colour strength. Transparency and colour purity remain unsatisfactory. Moreover, the production of mixed crystals (solid solutions) frequently entails reproducibility problems in terms of the quality, which may then have deleterious consequences for transparency and colour purity in particular, but also for colour strength and lightfastness.

The object of the present invention, accordingly, is to provide red organic pigments in colour filters for LCDs that do not have these disadvantages.

The invention accordingly provides for the use of fluorine-substituted perylenes in colour filters for LCDs. Equivalent thereto is a method of pigmenting colour filters for LCDs that is characterized in that the colour filter is pigmented with fluorine-substituted perylenes. All preferred embodiments for the use are also intended below to apply for the method of pigmenting. Preferred fluorine-substituted perylenes are of the formula (I)

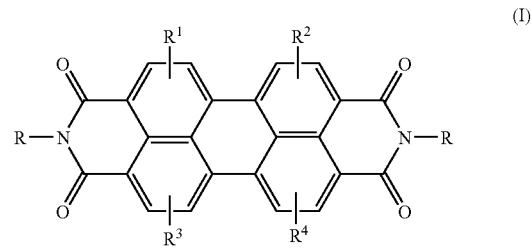

(I)

in which
R is H or is an optionally substituted organic radical,
$R^1$, $R^2$, $R^3$ and $R^4$ independently of one another are H, F, Cl or Br or are an optionally substituted organic radical, and at least one of the radicals R, $R^1$, $R^2$, $R^3$ and $R^4$ is fluorine or comprises at least one fluorine atom.

Particular preference is given to perylenes of the formula (I) in which
R is an organic radical substituted by one or more fluorine atoms and
$R^1$, $R^2$, $R^3$ and $R^4$ have the above definition.
In other words $R^1$-$R^4$ are preferably H.

"Organic radical" in the definition of R is preferably $C_1$-$C_8$-alkyl, more particularly methyl, or $C_6$-$C_{10}$-aryl optionally substituted by $C_1$-$C_8$-alkyl, phenoxy and/or $C_1$-$C_8$-alkoxy, substituted in each case by one or more fluorine atoms.

Particularly preferred perylenes of the formula (I) are those which are of the formula (Ia)

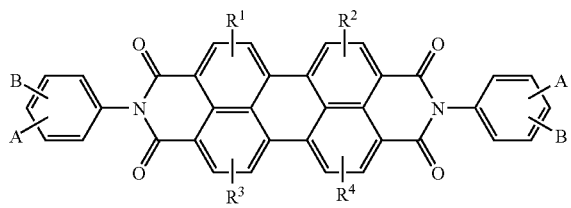

(Ia)

in which

A is fluorine or an organic radical substituted by one or more fluorine atoms,

B is H, F, Cl or Br or is an optionally substituted organic radical which may optionally together with A form a ring, or the radicals A and B, together with the C atoms of the phenyl ring to which they are attached, form a fused ring, and $R^1$, $R^2$, $R^3$ and $R^4$ have the definition given above.

Preferred organic radical substituted by fluorine atoms, in the definition of A and B, is $C_1$-$C_8$-alkyl, $C_1$-$C_8$-alkoxy, phenyl or phenoxy, each of which is substituted by one or more fluorine atoms.

In the formula (Ia) $R^1$, $R^2$, $R^3$ and $R^4$ are preferably hydrogen or fluorine, the radical B is H or optionally is fluorine-substituted $C_1$-$C_8$-alkyl, more particularly methyl or trifluoromethyl, and A is fluorine or is $C_1$-$C_8$-alkyl, more particularly methyl, $C_1$-$C_8$-alkoxy, more particularly methoxy, phenyl or phenoxy, each of which is preferably substituted by one or more fluorine atoms, or A and B together are a bridge member of the formula —O—$CF_2$—O—, —O—$CF_2$—$CF_2$—O—, —O—CHF—CHF—O— or —O—$CF_2$—$CF_2$—$CF_2$—O—.

Likewise preferably A and B together form a bridge which is substituted by one or more fluorine atoms and which with two adjacent C atoms of the benzene ring forms a five-, six- or seven-membered ring which is carbocyclic or may contain heteroatoms such as O, S or N.

Suitable fluorine-substituted $C_1$-$C_8$-alkyl radicals or $C_1$-$C_8$-alkoxy radicals are, for example, methyl, ethyl or optionally branched propyl, butyl, pentyl, hexyl or octyl radicals or the corresponding alkoxy radicals which carry at least one fluorine atom. Examples are fluoromethyl, trifluoromethyl, 2-fluoroethyl, 2,2,2-trifluoroethyl, pentafluoroethyl, 2,2,3,3-tetrafluoropropyl, perfluorobutyl, perfluorooctyl, especially perfluoro-n-octyl, and the corresponding alkoxy radicals.

Suitable fluorine-substituted phenyl or phenoxy radicals are, for example, 2-, 3- or 4-fluorophenyl or -phenoxy, 2,4- or 3,4-difluorophenyl or -phenoxy, pentafluorophenyl or -phenoxy.

Suitable optionally substituted organic radicals as a possible definition of B are preferably organic radicals substituted by one or more fluorine atoms, especially those which independently of A have the same definition as the radical A. Particularly preferred are the preferred definitions of A, especially trifluoromethyl.

Employed with more particular preference in accordance with the invention are pigments of the formulae (II) to (XII)

(II)

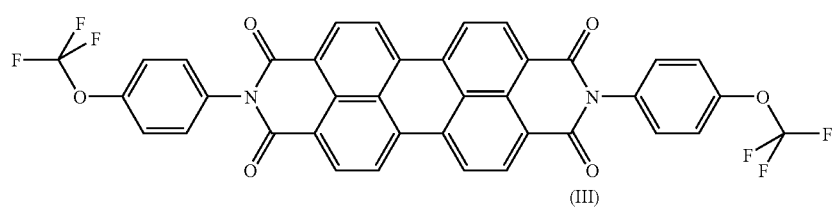

(III)

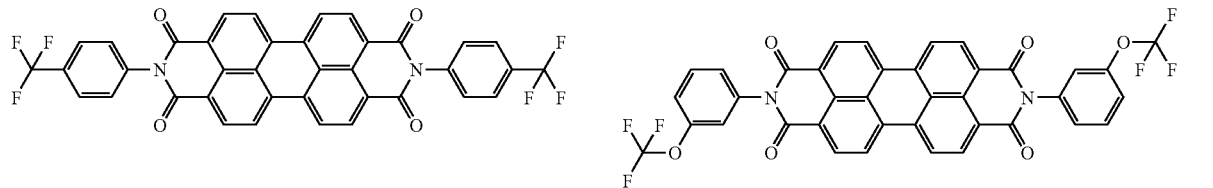

(IV)

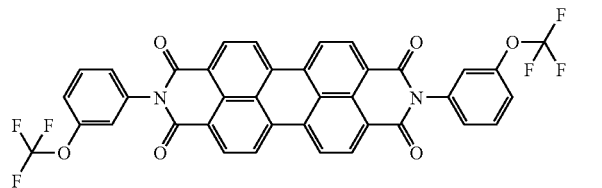

(V)

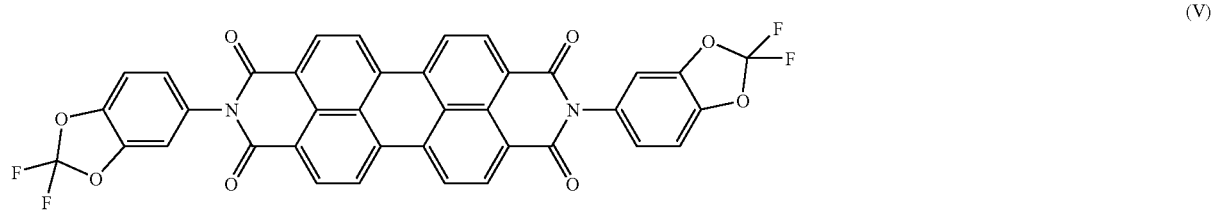

(VI)

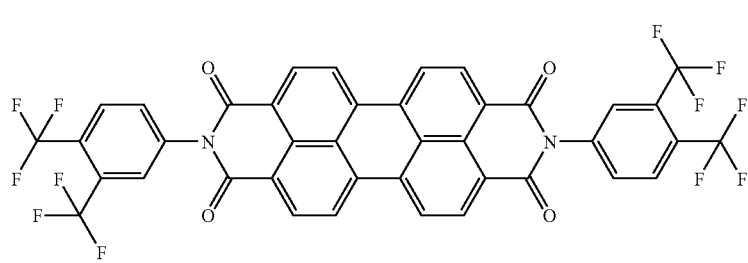

-continued

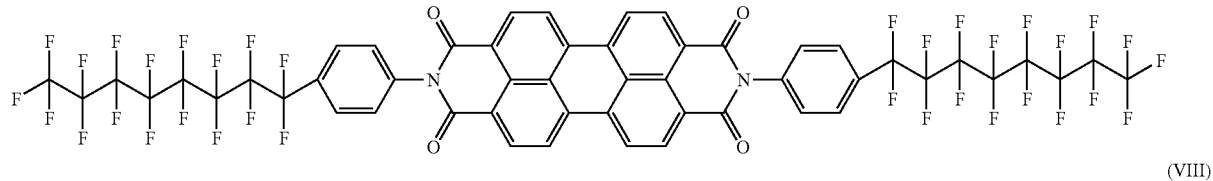

(VII)

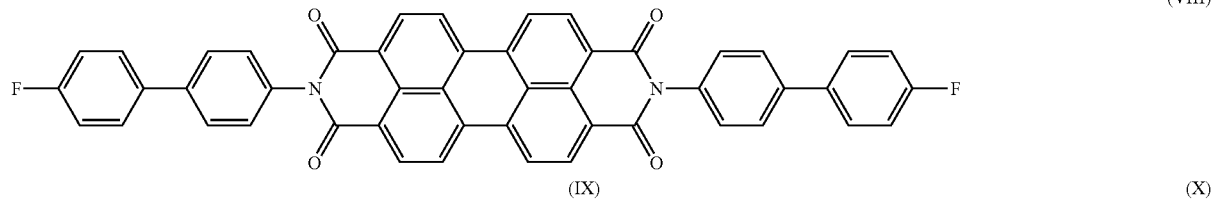

(VIII)

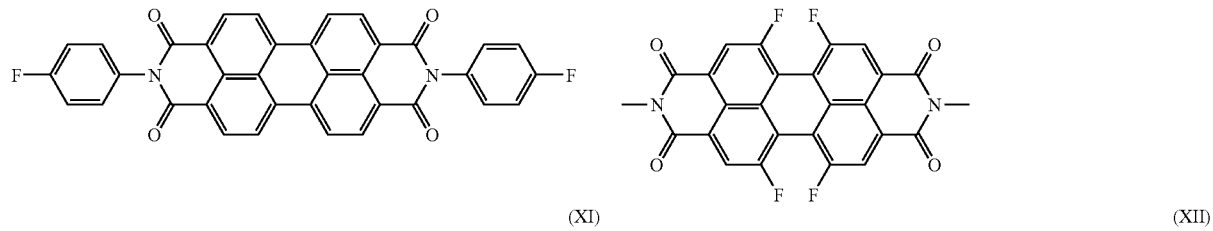

(IX) (X)

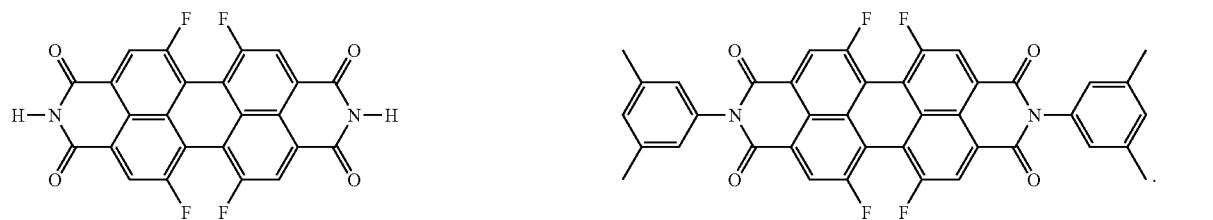

(XI) (XII)

The pigments used in accordance with the invention preferably possess a specific surface area of 40 to 200 m²/g, in particular of 60 to 140 m²/g, very preferably of 70 to 120 m²/g. The surface area is determined in accordance with DIN 66131: Determination of the specific surface area of solids by gas adsorption by the method of Brunauer, Emmett and Teller (B.E.T.).

The pigments used in accordance with the invention preferably possess a dispersion harshness of 10 to 500, in particular of 20 to 250, measured according to DIN 53775, part 7, the temperature of cold rolling being 25° C. and the temperature of hot rolling being 150° C. All of the dispersion harshnesses reported in this specification were determined in accordance with this modified DIN specification.

The pigments used in accordance with the invention preferably possess a particle size (longitudinal axis in the transmission electron microscope) of 10 to 200 nm, in particular of 20 to 100 nm. Preferably the pigments used in accordance with the invention possess a narrow particle size distribution with a relative standard deviation (standard deviation/particle size)<50%, especially <35%, more preferably <20%. Preferably the pigments used in accordance with the invention possess a length-to-width ratio of 5:1 to 1:1, in particular of 3:1 to 1:1, more preferably of 2:1 to 1.2:1.

The particle size and surface area of the pigments used in accordance with the invention can be adjusted by methods which are known per se and are set out, for example, in U.S. Pat. No. 6,068,695, such as, for example, salt kneading or ball milling and/or optionally downstream finishing steps such as, for example, heat treatments in aqueous, organic or aqueous/organic solvents with or without addition of additives.

The perylene pigments, especially those of the formula (I), used in accordance with the invention can also be employed in combination with other pigments, for the purpose, for example, of optimizing the optical properties of the colour fillers. The invention does not impose any restriction on the selection of other pigments for possible additional use. Both organic and inorganic pigments are suitable.

Preferred organic pigments are, for example, those of the monoazo, disazo, laked azo, β-naphthol, Napthol AS, benzimidazolone, quinacridone, disazo condensation, azo metal complex, isoindoline and isoindolinone series, and also polycyclic pigments such as, for example, from the phthalocyanine, quinacridone, perylene, perinone, thioindigo, anthraquinone, dioxazine, quinophthalone and diketopyrrolopyrrole series. In addition, laked dyes, especially Ca, Mg and Al lakes of dyes containing sulphonic or carboxylic acid groups. With very particular preference, the melamine-intercalated nickel complex of azobarbituric acid is claimed as a pigment for accompanying use.

Examples of other organic pigments which are intended for optionally accompanying use are:

Colour Index Pigment Yellow 12, 13, 14, 17, 20, 24, 74, 83, 86, 93, 94, 109, 110, 117, 125, 137, 138, 139, 147, 148, 150, 153, 154, 166, 173, 185, Colour Index Pigment Orange 13, 31, 36, 38, 40, 42, 43, 51, 55, 59, 61, 64, 65, 71, 72, 73, Colour Index Pigment Red 9, 97, 122, 123, 144, 149, 166, 168, 177, 179, 180, 192, 215, 216, 224, 254, 272, Colour Index Pigment Green 7, 10, 36, 37, 45, 58
Colour Index Pigment Blue 15, 15:1, 15:2, 15:3, 15:4, 15:6, 16,
Colour Index Pigment Violet 19, 23.

Further pigments not known from the Colour Index are, for example, the melamine-intercalated nickel-azobarbituric acid complex pigment of the formula

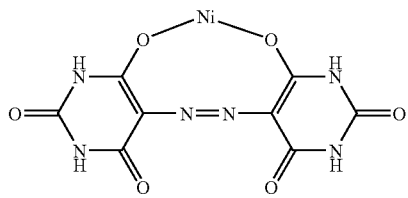

and also its tautomeric forms, known from DE102005033581, especially Example 2.

Mention may likewise be made of sulphonated derivatives of the pigments, especially those of the formula (I), used in accordance with the invention.

Where "other pigments"—other than the fluorine-substituted perylenes, especially those of the formula (I)—are used additionally, the fraction of "pigment" as defined above, conforming to the formula (I), is preferably 1-99% by weight, in particular 20-80% by weight, based on the total amount employed of all pigments.

Pigments preferred for accompanying use are Pigment Red 122, Pigment Red 149, Pigment Red 177, Pigment Red 179, Pigment Red 254, Pigment Violet 19, Pigment Yellow 138, Pigment Yellow 139, Pigment Yellow 150 or a melamine-intercalated nickel-azobarbituric acid complex pigment.

Particular preference is given to the use of pigment mixtures comprising, in addition to at least one fluorine-substituted perylene, in particular at least one pigment of the formula (I), at least one further red pigment from the group consisting of C.I. Pigment Red 122, C.I. Pigment Red 149, C.I. Pigment Red 177, C.I. Pigment Red 179, C.I. Pigment Red 254 and C.I. Pigment Violet 19 in colour filters for LCDs.

This mixture for preferred use optionally comprises additionally one or more yellow pigments or orange pigments.

The yellow or orange pigments used accompanyingly preferably possess an absorption band in the range from 400 to 520 nm.

In particular this preferred mixture comprises yellow pigments selected from the group consisting of C.I. Pigment Yellow 138, C.I. Pigment Yellow 139, C.I. Pigment Yellow 150 and a melamine-intercalated nickel-azobarbituric acid complex pigment.

The mixtures per se are likewise provided by this invention.

Preferred mixtures comprise, in addition to at least one fluorine-substituted perylene, preferably those of the formula (I), more particularly in addition to a pigment of the formula (Ia), at least one further red pigment from the group consisting of C.I. Pigment Red 122, C.I. Pigment Red 149, C.I. Pigment Red 177, C.I. Pigment Red 179, C.I. Pigment Red 254 and C.I. Pigment Violet 19.

Where yellow or orange pigments are used as "other pigments", the fraction of these yellow or orange "other pigments" is preferably 1% to 50% by weight, in particular 5%-30% by weight, based on the total amount employed of all pigments.

Where red pigments are used as "other pigments", the fraction of these red "other pigments" is preferably 1 to 99% by weight, in particular 20%-80% by weight, based on the total amount employed of all pigments.

The colour filters produced with the pigments of the invention or mixtures thereof are notable in particular for high colour purity and excellent transparency.

Likewise with preference the fluorine-substituted perylenes, especially those of the formula (I), are used in the form of a mixture which additionally also comprises at least one yellow pigment. Preferably those yellow pigments which possess an absorption band in the range from 400 to 520 nm. In particular this preferred mixture comprises yellow pigments selected from the group consisting of C.I. Pigment Yellow 138, C.I. Pigment Yellow 139, C.I. Pigment Yellow 150 and a melamine-intercalated nickel-azobarbituric acid complex pigment. These mixtures per se as well are likewise provided by this invention.

The invention further provides new perylenes of the formula (II), (IV) and (V), that of the formula (II) being particularly preferred.

The inventive use of the above-described pigments or pigment mixtures for producing colour filters for liquid-crystal displays will be described below with reference to the example of the pigment dispersion method according to the photoresist method.

The inventive use of the fluorine-substituted perylenes, not least pigments of the invention, for producing colour filters is characterized for example in that the pigment, optionally with a binder resin and an organic solvent, optionally with addition of a dispersant, is homogenized and then subjected to continuous or batchwise wet-comminution, to a particle size by number (electron-microscopic determination) of 99.5%<1000 nm, preferably 95%<500 nm and in particular 90%<200 nm. Suitable wet-comminution methods include, for example, stirrer or dissolver dispersion, grinding by means of stirred ball mills or bead mills, kneaders, roll mill, high-pressure homogenization or ultrasonic dispersion.

The dispersing treatment is accompanied or followed by the addition of at least one photocurable monomer and a photoinitiator. Following dispersion, further binder resin, solvent or customary photoresist adjuvants may be introduced as is necessary for the desired photosensitive coating formulation (photoresist) for producing the colour filters. For the purposes of this invention, a photoresist is a formulation comprising at least one photocurable monomer and a photoinitiator in addition to the fluorine-substituted perylene, in particular to the perylene of the formula (I).

Useful dispersants include generally commercially available dispersants, such as polymeric, ionic or nonionic dispersants, based for example on polycarboxylic acids or polysulphonic acids, and also polyethylene oxide-polypropylene oxide block copolymers. Derivatives of organic dyes can also be used, furthermore, as dispersants or co-dispersants.

The production of colour filters therefore initially gives rise to "preparations" which comprise, based on the preparation:
  at least one fluorine-substituted perylene, especially a perylene of the formula (I), referred to for the purposes of this specification as pigment of the invention,
  optionally one or more other pigments,
  optionally a binder resin,
  at least one organic solvent, and
  optionally a dispersant.

In one preferred embodiment the preparation contains (amounts based on preparation):
1-50% by weight of at least one fluorine-substituted perylene, especially a perylene of the formula (I)
0-50% by weight of one or more other pigments
0-20% by weight of binder resin 0-20% by weight of dispersant
10-94% by weight of organic solvent.

The coating of the photoresist onto a plate to produce the coloured image element patterns can be carried out by either direct or indirect application. Examples of application methods that may be mentioned include ink jet, roller coating, spincoating, spray coating, dip coating and air knife coating.

Examples of suitable plates include, depending on use, the following: transparent glasses such as white or blue glass plate, silicate-coated blue glass plate, synthetic resin plate or synthetic resin films based for example on polyester resin, polycarbonate resin, acrylic resin or vinyl chloride resin, and additionally metal plates based on aluminium, copper, nickel or steel, and also ceramic plates or semiconductor plates with photoelectric transfer elements applied.

Application is generally effected in such a way that the photosensitive layer obtained is 0.1 to 10 µm thick.

Application may be followed by thermal drying of the layer.

Exposure takes place preferably by exposing the photosensitive layer to an active light beam in the form, preferably, of an image pattern by means of photomask. This cures the layer at the exposed areas. Examples of suitable light sources include the following: high-pressure and ultrahigh-pressure mercury vapour lamp, xenon lamp, metal halide lamp, fluorescent lamp, and laser beam in the visible region.

Development following exposure removes the unexposed portion of the coating, to give the desired image pattern form of the colour elements. Customary development methods include spraying with or dipping in aqueous alkaline developer solution or in an organic solvent that contains inorganic alkali such as, for example, sodium hydroxide or potassium hydroxide, sodium metasilicate or organic bases such as monoethanolamine, diethanolamine, triethanolamine, triethylamine or salts thereof.

Development is generally followed by thermal afterdrying/-curing of the image patterns.

As binder resins which can be used together with the "pigment" or pigment formulations based thereon (i.e. containing binder resin and pigment of the formula (I)) in colour filters or in the preparations for producing colour filters by, for example, the pigment dispersion method, the invention imposes no particular restriction; conventional film-forming resins in particular are suitable for application in colour filters.

By way of example, binder resins from the group of the cellulose resins such as carboxymethyl-hydroxyethylcellulose and hydroxyethylcellulose, acrylic resins, alkyd resins, melamine resins, epoxy resins, polyvinyl alcohols, polyvinylpyrrolidones, polyamides, polyamide-imines and polyimides are suitable.

Suitable binder resins also include those containing photopolymerizable, unsaturated bonds. The binder resins may for example be resins from the group of the acrylic resins. Mention may be made in this case in particular of homopolymers and copolymers of polymerizable monomers such as methyl (meth)acrylate, ethyl (meth)acrylate, propyl (meth)acrylate, butyl (meth)acrylate, styrene and styrene derivatives, for example, and additionally copolymers between carboxyl-bearing polymerizable monomers such as (meth)acrylic acid, itaconic acid, maleic acid, maleic anhydride, maleic acid monoalkyl esters, particularly with alkyl of 1 to 12 carbon atoms, and polymerizable monomers such as (meth)acrylic acid, styrene and styrene derivatives, such as α-methylstyrene, m- or p-methoxystyrene, p-hydroxystyrene, for example. Examples that may be mentioned are reaction products of carboxyl-containing polymeric compounds with compounds which contain in each case one oxirane ring and an ethylenically unsaturated compound such as, for example, glycidyl (meth)acrylate, acryloyl glycidyl ether and itaconic acid monoalkylglycidyl ethers, etc., and also reaction products of carboxyl-containing polymeric compounds with compounds each containing one hydroxyl group and an ethylenically unsaturated compound (unsaturated alcohols), such as allyl alcohol, 2-buten-4-ol, oleyl alcohol, 2-hydroxyethyl (meth)acrylate, N-methylolacrylamide, etc.; binder resins of this kind may further also comprise unsaturated compounds which possess free isocyanate groups.

In general the equivalence of the unsaturation (molar weight of binder resin per unsaturated compound) of the said binder resins is 200 to 3000, in particular 230 to 1000, to provide not only adequate photopolymerizability but also film hardness. The acid value is generally 20 to 300, in particular 40 to 200, to provide sufficient alkali developability following exposure of the film.

The average molar weight of the binder resins to be used is between 1500 and 200 000, in particular 10 000 to 50 000 g/mol.

The organic solvents used in the context of the inventive use of the formulation for colour filters are, for example, ketones, alkylene glycol ethers, alcohols and aromatic compounds. Examples are, from the group of the ketones: acetone, methyl ethyl ketone, cyclohexanone, etc.; from the group of the alkylene glycol ethers: methylcellosolve (ethylene glycol monomethyl ether), butylcellosolve (ethylene glycol monobutyl ether), methylcellosolve acetate, ethylcellosolve acetate, butylcellosolve acetate, ethylene glycol monopropyl ether, ethylene glycol monohexyl ether, ethylene glycol dimethyl ether, diethylene glycol ethyl ether, diethylene glycol diethyl ether, propylene glycol monomethyl ether, propylene glycol monoethyl ether, propylene glycol monopropyl ether, propylene glycol monobutyl ether, propylene glycol monomethyl ether acetate, diethylene glycol methyl ether acetate, diethylene glycol ethyl ether acetate, diethylene glycol propyl ether acetate, diethylene glycol isopropyl ether acetate, diethylene glycol butyl ether acetate, diethylene glycol tert-butyl ether acetate, triethylene glycol methyl ether acetate, tri-ethylene glycol ethyl ether acetate, triethylene glycol propyl ether acetate, triethylene glycol iso-propyl ether acetate, triethylene glycol butyl ether acetate, triethylene glycol tert-butyl ether acetate, etc.; from the group of the alcohols: methyl alcohol, ethyl alcohol, isopropyl alcohol, n-butyl alcohol, 3-methyl-3-methoxybutanol, etc.; and, from the group of the aromatic solvents, benzene, toluene, xylene, N-methyl-2-pyrrolidone, ethyl N-hydroxymethyl-2-acetate, etc.

Further other solvents are 1,2-propanediol diacetate, 3-methyl-3-methoxybutyl acetate, ethyl acetate, tetrahydrofuran, etc. The solvents can be used individually or in mixtures with one another.

The invention further provides a photoresist comprising at least one pigment as defined above or at least one pigment formulation of the invention and at least one photocurable monomer and also at least one photoinitiator.

The photocurable monomers contain at least one reactive double bond and optionally other reactive groups in the molecule.

Photocurable monomers may be interpreted in this context as being, in particular, reactive solvents or what are called reactive diluents from the group, for example, of the mono-, di-, tri- and multifunctional acrylates and methacrylates, vinyl ethers, and glycidyl ethers. Suitable reactive groups additionally present include allyl, hydroxyl, phosphate, urethane, secondary amine and N-alkoxymethyl groups. Monomers of this kind are known to the skilled person and are listed for example in *[Römpp Lexikon, Lacke und Druckfarben*, Dr. Ulrich Zorll, Thieme Verlag Stuttgart-New York, 1998, pp. 491/492] or under the entry heading 'Reaktivverdünner' [Reactive diluents].

The selection of the monomers is guided in particular by the nature and intensity of the exposing radiation used, the desired reaction with the photoinitiator, and the film properties. Monomer combinations can also be used.

Photoreaction initiators or photoinitiators may be understood as being compounds which by absorbing visible or ultraviolet radiation form reactive intermediates that are capable of inducing a polymerization reaction on the part, for example, of the abovementioned monomers and/or binder resins. Photoreaction initiators are likewise general knowledge and may likewise be taken from *[Römpp Lexikon, Lacke und Druckfarben*, Dr. Ulrich Zorll, Thieme Verlag Stuttgart-New York, 1998, pp. 445/446] or under the entry heading 'Photoinitiatoren' [Photoinitiators].

The invention imposes no restriction with regard to the photocurable monomers or photoinitiators that are to be employed.

The invention preferably provides photoresists comprising
A) at least one "pigment" as defined above, in particular in a mixture with other pigments, or a pigment formulation of the invention that is based thereon,
B1) at least one photocurable monomer,
B2) at least one photoinitiator,
C1) optionally an organic solvent,
D) optionally a dispersant,
E) optionally a binder resin,
and optionally further additions.

The invention also imposes no restriction with regard to the technology for generating the coloured image element patterns on the basis of the pigments for use in accordance with the invention or solid pigment formulations. In addition to the above-described photolithographic method, other methods such as offset printing, chemical milling or ink-jet printing are also suitable. The selection of suitable binder resins and solvents or pigment vehicles, and of further additions, should be conformed to the particular method. In the case of the ink-jet method, which comprehends not only thermal but also mechanical and piezomechanical ink-jet printing, suitable vehicles for the pigments and optionally binder resins include not only purely organic vehicles but also aqueous-organic vehicles; aqueous-organic vehicles are in fact preferred, with suitable organic solvents being those specified above.

The invention further provides colour filters characterized in that they comprise at least one fluorine-substituted perylene pigment, preferably a pigment of the formula (I), more particularly a pigment of the formula (Ia). Especially preferred colour filters comprise at least one pigment of the formula (II), (IV) or (V). Generally speaking a colour filter is a photoresist which is cured on a support, supports including not only glass but also other substrates such as polymeric, metallic or ceramic plates.

The invention also provides liquid-crystal displays comprising at least one colour filter of the invention.

EXAMPLES

Example 1 a) Synthesis

At 80° C., 200 g of phenol were introduced. Added thereto was 0.1 mol of perylenetetracarboxylic dianhydride (per acid) and 0.3 mol of diethanolamine, and the batch was heated to 120° C. in 30 minutes. It was admixed with 0.225 mol of p-trifluoromethoxyaniline and then heated at 150° C. for 5 hours with distillative removal of phenol/water. Subsequently the batch was cooled indirectly to 90° C. and 280 g of methanol were added dropwise. This was followed by cooling to 40° C. and isolation. The product was washed with 500 g of methanol and then with 500 g of water.

The moist presscake was introduced into 800 ml of 5% strength KOH solution, this system was heated to 80° C. and stirred for 1 hour, and the product was isolated, washed to neutrality with water and dried. The product was dissolved in 1500 g of sulphuric acid at 20° C. and discharged slowly at about 60° C. onto 2000 ml of methanol. The mixture was diluted with water and the product was isolated by filtration, washed and dried.

Yield: 95% of perylene of the formula (II)

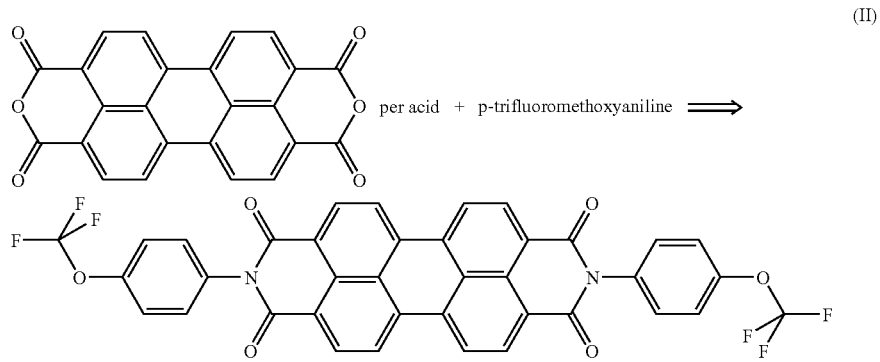

BET: 44 m²/g b) Production of the PVC Sample for Determining the Hue and the Dispersion Harshness For determining the dispersion harshness, 100 g of PVC paste, prepared from 4.2 parts of Vestolit® E 7004 (emulsion-PVC powder), 1.8 parts of diisooctyl phthalate, 0.15 part of Baerostab® UBZ 770 (liquid barium-zinc stabilizer) and 0.125 part of Moltopren® white paste RUN 01 (pigment formulation containing 50% TiO₂), were applied at 150° C. to a Collin laboratory mixing roll mill. The roll nip was 0.8 mm.

0.1 g of the sample was applied to the PVC sheet and the roll nip was set to 0.12 mm. The rolled sheet was taken off and applied again. This operation was repeated eight times. The roll nip was set to 0.8 mm and the rolled sheet was removed. A test specimen measuring 60×60 mm was punched from the roiled sheet.

The remainder of the sheet was then applied to the roll mill at 25° C. The roll nip was 0.2 mm. The rolled sheet was taken off and applied again. This process was repeated 15 times. The sheet, which is no longer smooth from the cold rolling, was applied to the roll at 150° C. with a roll nip of 0.8 mm. After 60 s, the sheet was removed and a test specimen measuring 60×60 mm was punched from it. The rotational speed of the roll was held at a constant 20 rpm and the friction at 1:1.1.

The dispersion harshness is the percentage increase in colour strength after rolling at 25° C. Dispersion harshness: 38

The transparent test specimens were produced in the same way, but using a test paste consisting of 4.2 parts of Vestolit® E 7004 (emulsion-PVC powder), 1.8 parts of diisooctyl phthalate and 0.15 part of Baerostab® URZ 770 (liquid barium-zinc stabilizer).

The hues were determined using a Gretag Macbeth spectrometer.

The samples were subjected to measurement with a 10° observer angle, D65 illuminant, without a gloss trap:

Reflection measurements:

$L^*$: 62.18 $a^*$: 46.96 $b^*$: 4.63 $C^*$: 47.19 $h°$: 5.63

The pigments of the formula (III) to (IX) were prepared as for Example 1.

USE EXAMPLES

Preparation of a Red Formulation and its Use for Producing a Red Colour Filter

Use Example 1

Inventive

Pigment used: Pigment from Example 1

In a stirred vessel 774 parts by weight of methoxybutyl acetate and 286 parts by weight of a 21% strength solution of an alkali-soluble copolymer (binder resin) based on benzyl methacrylate (70 parts)/2-hydroxyethyl methacrylate (15 parts)/methacrylic acid (15 parts), molar weight around 25 000 g/mol, in methoxypropyl acetate were mixed homogeneously. This gave a 'formulation'.

Subsequently 100 parts by weight of pigment from Example 1, dried beforehand at 70° C. to a residual moisture content of less than 1% by weight, were introduced homogeneously into the formulation.

The pigment suspension was ground in a horizontal, closed bead mill using yttrium-stabilized zirconium oxide beads (diameter 0.6 to 1.0 mm).

Preparation of a Photoresist

Introduced homogeneously with stirring into 1000 parts by weight of the resulting formulation were 34.5 parts by weight of trimethylolpropane triacrylate (monomeric reactive diluent) and 13.8 parts by weight of a photoreaction initiator based on benzophenone and N,N'-tetraethyl-4,4'-diaminobenzophenone in a ratio of 3/1 parts by weight.

This gave a UV-curable photoresist, which was applied to a transparent substrate and developed to give the colour filter.

For this purpose the photoresist was spin-coated onto a section of cleaned borosilicate glass (Corning® 7059, Owens Corning Corp.) measuring 300×350 mm and was dried at 110° C. for 5 minutes in an oven under clean conditions to give a film approximately 1.5-2 μm thick.

The film, after cooling, was then UV-exposed at a dose of 200 mJ/cm$^2$ with an ultra-high-pressure mercury vapour lamp, by means of a negative mask to obtain the desired stripe image pattern, and then developed by means of 0.06% strength aqueous potassium hydroxide solution at room temperature, cleaned with fully demineralized water and dried. This was followed by a 30-minute aftercure at 235° C. in an oven under clean conditions.

The resulting red, inventive colour filter 1, relative to the non-inventive colour filter 2, produced in accordance with Use Example 2, possessed a significantly improved spectral transparency. The colour purity and brilliance of colour filter 1 are excellent.

Use Example 2

Not Inventive

Pigment used: Pigment Red 149

In the same way as for Use Example 1, 100 parts by weight of Pigment Red 149, which had been dried beforehand at 70° C. to a residual moisture content of less than 1% by weight, were introduced homogeneously into the formulation from Use Example 1.

The resulting pigment suspension was ground in a horizontal, closed bead mill, using yttrium-stabilized zirconium oxide beads, in the same way as in Use Example 1.

The photoresist was likewise produced in the same way as in Use Example 1.

Use Example 3

Inventive

Pigment used: 80% of pigment from Example 1

20% of melamine-intercalated nickel-azobarbituric acid pigment, prepared according to Example 2 from DE 10 2005 033 581.

The preparation of a red formulation and its use for producing a red colour filter took place in the same way as in Use Example 1.

A photoresist produced as described in Use Example 1, and a red, inventive colour filter produced therewith, possessed very good spectral transparency properties and also excellent colour purity and brilliance.

Use Example 4

Inventive

In the same way as in Use Example 1, a colour filter was produced on the basis of the following pigment mixture.

Pigment used: 40% of pigment from Example 1

40% of C.I. Pigment Red 254

20% of melamine-intercalated nickel-azobarbituric acid pigment

The photoresist prepared and red, inventive colour filter produced therewith possessed very good spectral transparency properties and also excellent colour purity and brilliance.

The invention claimed is:

1. A method of pigmenting colour filters for LCD's comprising: pigmenting the colour filters with a pigment comprising at least one compound according to formula (II), (IV), and (V):

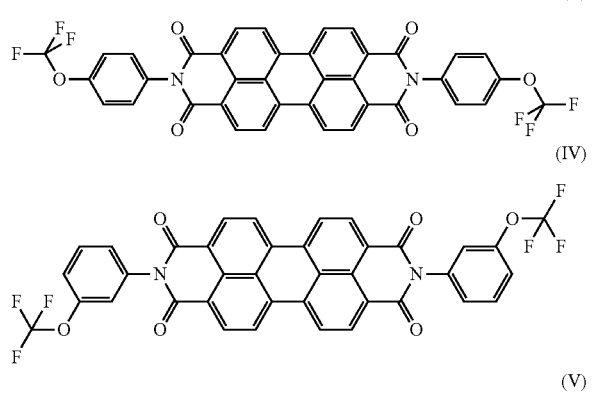

2. The method according to claim 1, characterized in that the pigment has a B.E.T. surface area of 40-200 m²/g.

3. Compounds of the formula (II), (IV) or (V) comprising:

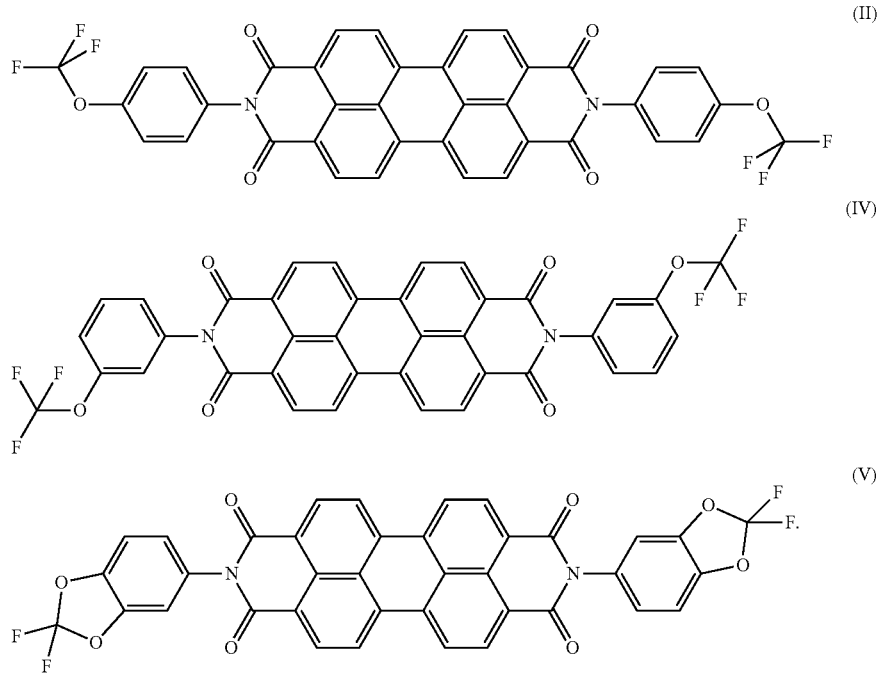

4. Photoresist comprising at least one photocurable monomer, at least one photoinitiator and at least one compound according to formula (II), (IV), and (V):

5. Colour filter comprising at least one fluorine-substituted perylene pigment according to formula (II), (IV), and (V):

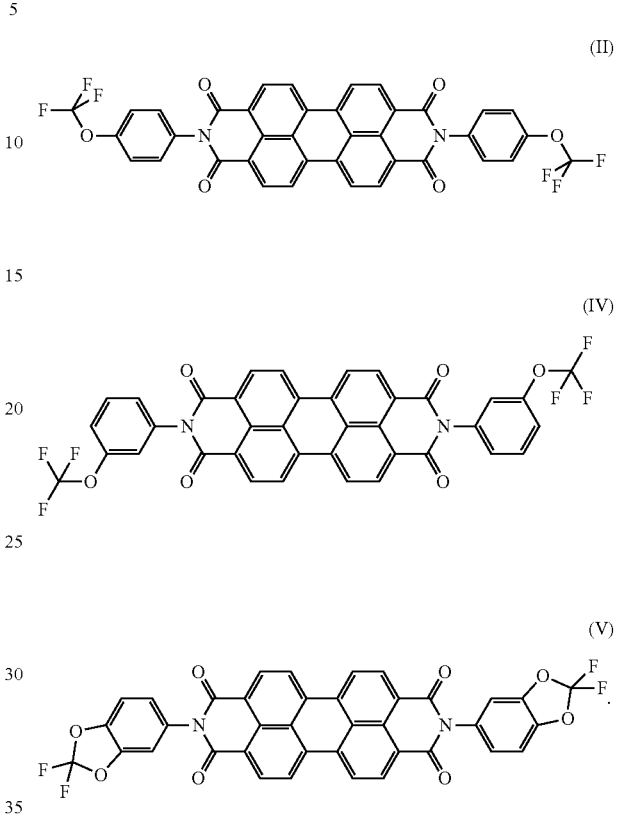

(II)
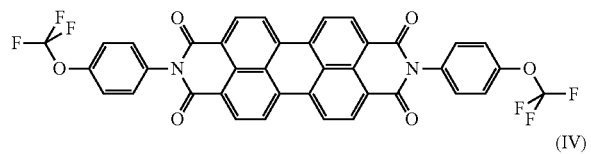

(IV)
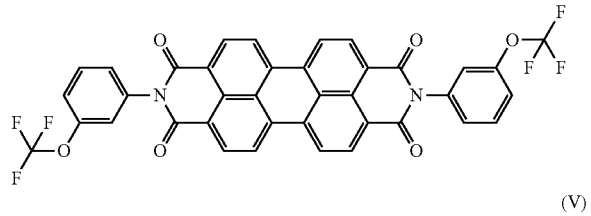

(V)
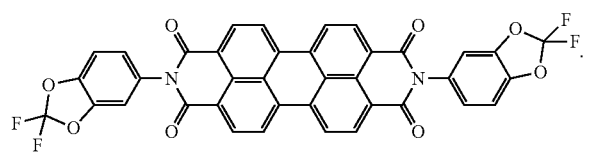

6. Liquid-crystal display comprising at least one colour filter according to claim 5.

7. Mixture comprising, at least one fluorine-substituted perylene according to formula (II), (IV), and (V):

(II)
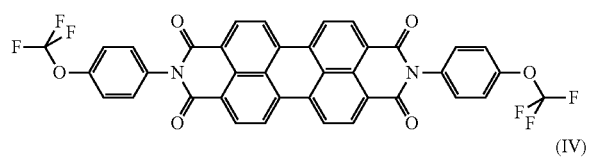

(IV)
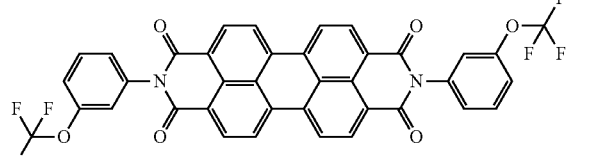

(V)
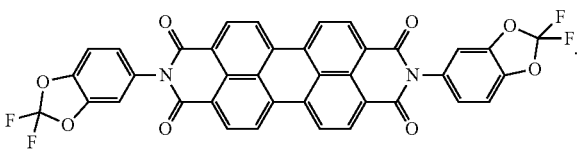

and at least one further red pigment selected from the group consisting of C.I. Pigment Red 122, C.I. Pigment Red 149, C.I. Pigment Red 177, C.I. Pigment Red 179, C.I. Pigment Red 254, and C.I. Pigment Violet 19.

8. Mixture according to claim 7, further comprising one or more yellow pigments or orange pigments which possess an absorption band in the range from 400 to 520 nm.

9. Mixture comprising, at least one fluorine-substituted perylene according to formula (II), (IV), and (V):

(II)
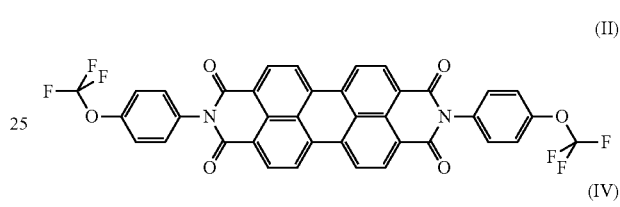

(IV)
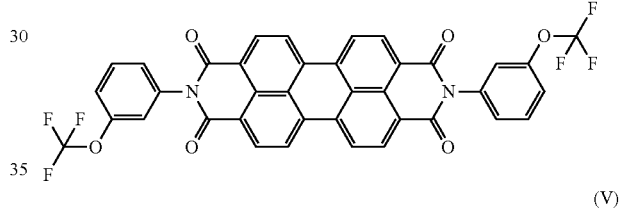

(V)
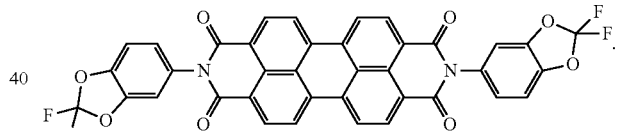

and at least one yellow pigment.

* * * * *